(12) United States Patent
Du Preez

(10) Patent No.: US 11,389,123 B2
(45) Date of Patent: Jul. 19, 2022

(54) METHOD FOR DETERMINING TREATMENT OF ORTHOPAEDIC IMBALANCES, AND APPARATUS THEREFOR

(71) Applicant: Lourens Russel Du Preez, Mosselbay (CA)

(72) Inventor: Lourens Russel Du Preez, Mosselbay (CA)

( * ) Notice: Subject to any disclaimer, the term of this patent is extended or adjusted under 35 U.S.C. 154(b) by 70 days.

(21) Appl. No.: 17/254,385

(22) PCT Filed: Mar. 15, 2019

(86) PCT No.: PCT/ZA2019/050010
§ 371 (c)(1),
(2) Date: Dec. 21, 2020

(87) PCT Pub. No.: WO2019/246638
PCT Pub. Date: Dec. 26, 2019

(65) Prior Publication Data
US 2021/0267559 A1    Sep. 2, 2021

(30) Foreign Application Priority Data

Jun. 20, 2018  (ZA) .................................. 201804108

(51) Int. Cl.
*A61C 19/045* (2006.01)
*A61B 6/14* (2006.01)
*A61B 6/00* (2006.01)

(52) U.S. Cl.
CPC .............. *A61B 6/14* (2013.01); *A61B 6/4291* (2013.01); *A61B 6/461* (2013.01)

(58) Field of Classification Search
CPC ......... A61B 6/14; A61B 6/4291; A61B 6/461; A61B 5/1178; A61B 5/1171;
(Continued)

(56) References Cited

U.S. PATENT DOCUMENTS 1,586,739 A    6/1926  Hanau
2,070,025 A    2/1937  Phillips
(Continued)

OTHER PUBLICATIONS

Search report and written opinion dated Dec. 26, 2019 in International Application Serial No. PCT/ZA2019/050010.

*Primary Examiner* — Don K Wong
(74) *Attorney, Agent, or Firm* — Haugen Law Firm PLLP

(57) ABSTRACT

A method for determining treatment of orthopaedic imbalances including the steps of: mounting upper and lower jaw dentition models to an articulator; setting the position of the models to replicate the relative positions of the jaw dentitions of a patient; determining from an x-ray or scan: (i) the outline of the patient's condylar head; and (ii) the pattern and depth of the patient's fossae; displaying a reproduction of the outline of the patient's condylar head; displaying a reproduction of the pattern and depth of the patient's fossae and eminance; adjusting the relative position of the models to remedy orthopaedic imbalances, which adjustment causes relative movement of: (i) the display of the condylar head; and (ii) the display of the pattern and depth of the fossae and eminance; and recording adjustments made to the relative position of the fossae/eminence and condoylar head and the upper and lower jaw dentition models.

9 Claims, 7 Drawing Sheets

(58) Field of Classification Search
CPC ... A61B 5/0082; A61B 5/0088; A61C 19/045; A61C 9/0066; A61C 11/00; A61C 9/0053; A61C 19/05; A61C 13/0004; A61C 9/0006; A61C 9/004

See application file for complete search history.

(56) References Cited

U.S. PATENT DOCUMENTS

| | | | |
|---|---|---|---|
| 2,909,837 | A | 10/1959 | Gerber |
| 3,159,915 | A | 12/1964 | Beu et al. |
| 3,431,649 | A | 3/1969 | Guichet |
| 4,058,895 | A | 11/1977 | Mack et al. |
| 4,290,754 | A | 9/1981 | Edwardson |
| 4,773,854 | A | 9/1988 | Weber |
| 5,073,109 | A | 12/1991 | El Hadary |
| 5,160,262 | A | 11/1992 | Alpern et al. |
| 7,534,105 | B2 | 5/2009 | Arai et al. |
| 10,524,886 | B2 * | 1/2020 | Kopelman ........... A61C 9/0066 |
| 2015/0111168 | A1 | 4/2015 | Vogel |
| 2018/0153658 | A1 | 6/2018 | Azer |

\* cited by examiner

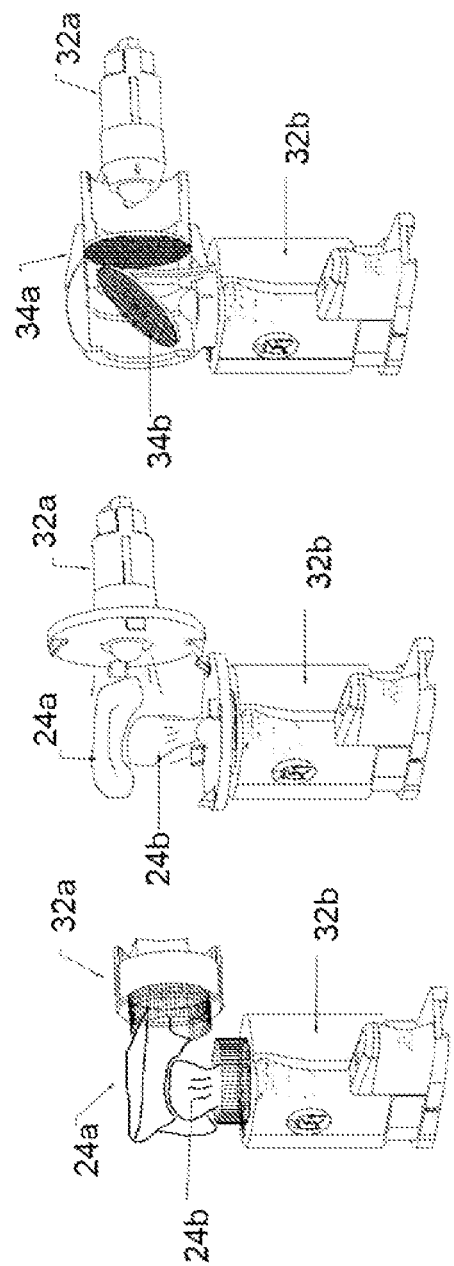

METHOD FOR DETERMINING TREATMENT OF ORTHOPAEDIC IMBALANCES, AND APPARATUS THEREFOR

BACKGROUND

The present invention relates to a method for determining treatment of orthopaedic imbalances, and apparatus therefor. More particularly, the invention relates to a method utilising an articulator and representations of: (i) the condylar head outline; and (ii) the pattern and depth of the fossae and eminance.

Various methods for determining treatment of orthopaedic imbalances are known. For instance, it is known for a dentist/dental surgeon to generate a 3D scan of the mandible and maxilla of a patient and to use software to determine the treatment of orthopaedic imbalances. It is also known for articulators to be set up accurately to reproduce movement of the mandible relative to the maxilla about the condylar joint.

For example, U.S. Pat. No. 1,586,739 "Dental articulator", U.S. Pat. No. 2,070,025 "Dental instrument", U.S. Pat. No. 2,909,837 "Articulator", U.S. Pat. No. 3,159,915 "Dental articulator", U.S. Pat. No. 3,431,649 "Dental face bow", U.S. Pat. No. 4,058,895 "Dental articulator", U.S. Pat. No. 4,290,754 "Articulator for use in the making of dentures or parts thereof", U.S. Pat. No. 4,773,854 "Device for the representation and correction of condylar motions" and U.S. Pat. No. 5,073,109 "Fully adjustable articulator device" describe articulators that record condylar positions.

A drawback of known methods using articulators for determining treatment of orthopaedic imbalances is that the articulators do not display both the condylar head outline and the pattern and depth of the fossae.

It is an object of the present invention to provide a method for determining treatment of orthopaedic imbalances utilising an articular with representations of both the condylar head outline and the pattern and depth of the fossae, to enable a dentist/dental surgeon directly to appreciate the affect adjustment of the articulator has on the relative position of the condoyle joint and fossae (as represented).

SUMMARY OF THE INVENTION

According to a first aspect of the present invention, there is provided a method for determining treatment of orthopaedic imbalances, which method includes the steps of:
  mounting upper and lower jaw dentition models to an articulator;
  setting the position of the upper and lower jaw dentition models substantially to replicate the relative positions of the upper and lower jaw dentitions of a patient;
  determining from one or more x-ray and/or scan: (i) the outline of the patient's condylar head; and (ii) the pattern and depth of the patient's fossae;
  displaying a substantial reproduction of the outline of the patient's condylar head;
  displaying a substantial reproduction of the pattern and depth of the patient's fossae and eminence;
  adjusting the relative position of the upper and lower jaw dentition models to remedy orthopaedic imbalances, which adjustment causes relative movement of: (i) the display of the condylar head; and (ii) the display of the pattern and depth of the fossae and eminence; and
  recording the adjustments made to the relative position of the fossae/eminence and condoylar head and the upper and lower jaw dentition models.

Typically, the method further includes the step of taking an impression of the bite of the upper and lower jaw dentition models after the relative position of the upper and lower jaw dentition models have been adjusted.

Generally, the steps of: (i) setting the position of the upper and lower jaw dentition models substantially to replicate the relative positions of the upper and lower jaw dentitions of a patient; and (ii) adjusting the relative position of the upper and lower jaw dentition models to remedy orthopaedic imbalances, comprises relative forward, backward, up, down, left, right, roll, yaw and pitch of the upper and lower jaw dentition models.

Preferably, templates are used to: (i) display a substantial reproduction of the outline of the patient's condylar head; and (ii) projection display the pattern and depth of the patient's fossae.

Typically, the outline of the patient's condylar head is displayed by a template stensil.

Generally, the step of displaying the pattern and depth of the patient's fossae comprises selecting from a series of photo projections pattern that best matches the pattern shape depth of the patient's fossae and securing the selected template pattern to the articulator.

Preferably, the template patterns are printed on a transparent template body.

According to a second aspect of the present invention, there is provided an articulator for use in the method according to the first aspect of the invention, which articulator includes:
  a light source;
  a grid on which the light source, in use, casts light; and
  a template that displays a shape representing: (i) the outline of a condylar head;
  or (ii) the pattern and depth of a fossae, which template is removably securable to the articulator.

Typically, the articulator includes mounts for securing upper and lower jaw dentition models thereto, and which articulator permits relative forward, backward, up, down, left, right, roll, yaw and pitch of the mounts.

BRIEF DESCRIPTION OF THE DRAWINGS

The invention will now be described in more detail, by way of example only, with reference to the accompanying drawings in which:

FIGS. 7(a)-(c) are perspective views of adapters which can be mounted on the articulator in FIG. 1.

DESCRIPTIONS OF A PREFERRED EMBODIMENT OF THE METHOD AND ARTICULATOR

Figure 1:
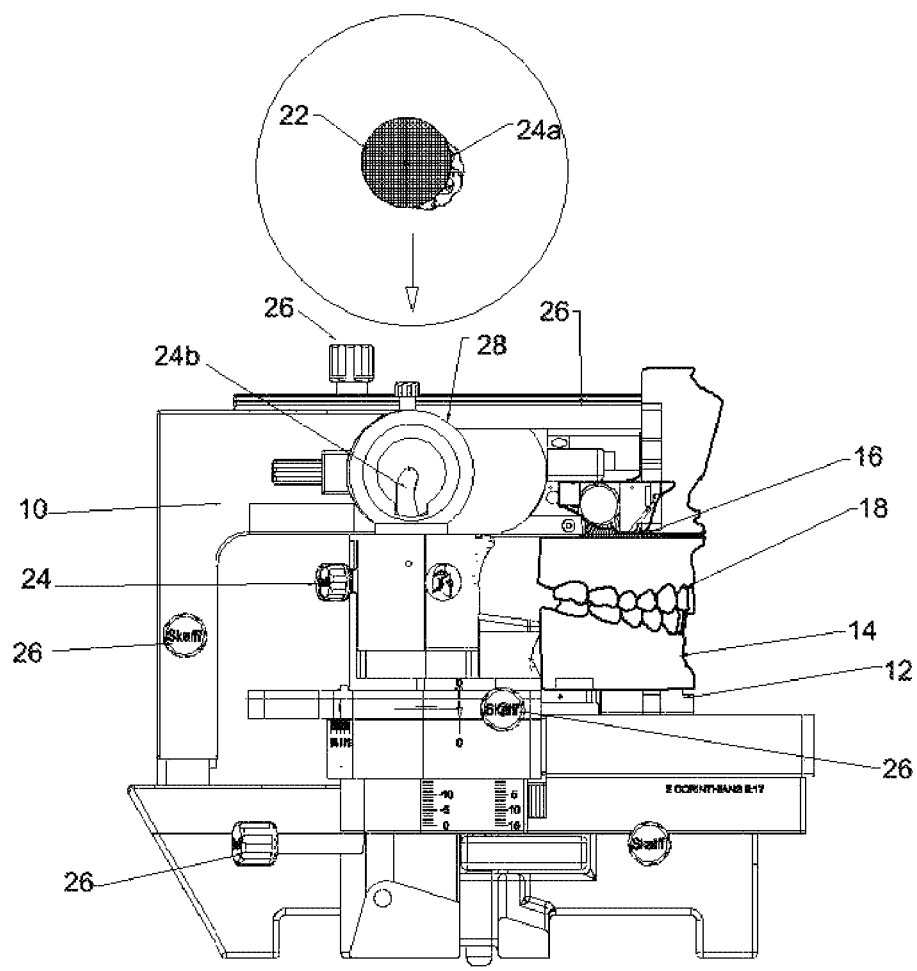
FIG. 1 is the side view of the articulator according to a second aspect of the present invention, with a projector shield in a raised position.
Figure 2:
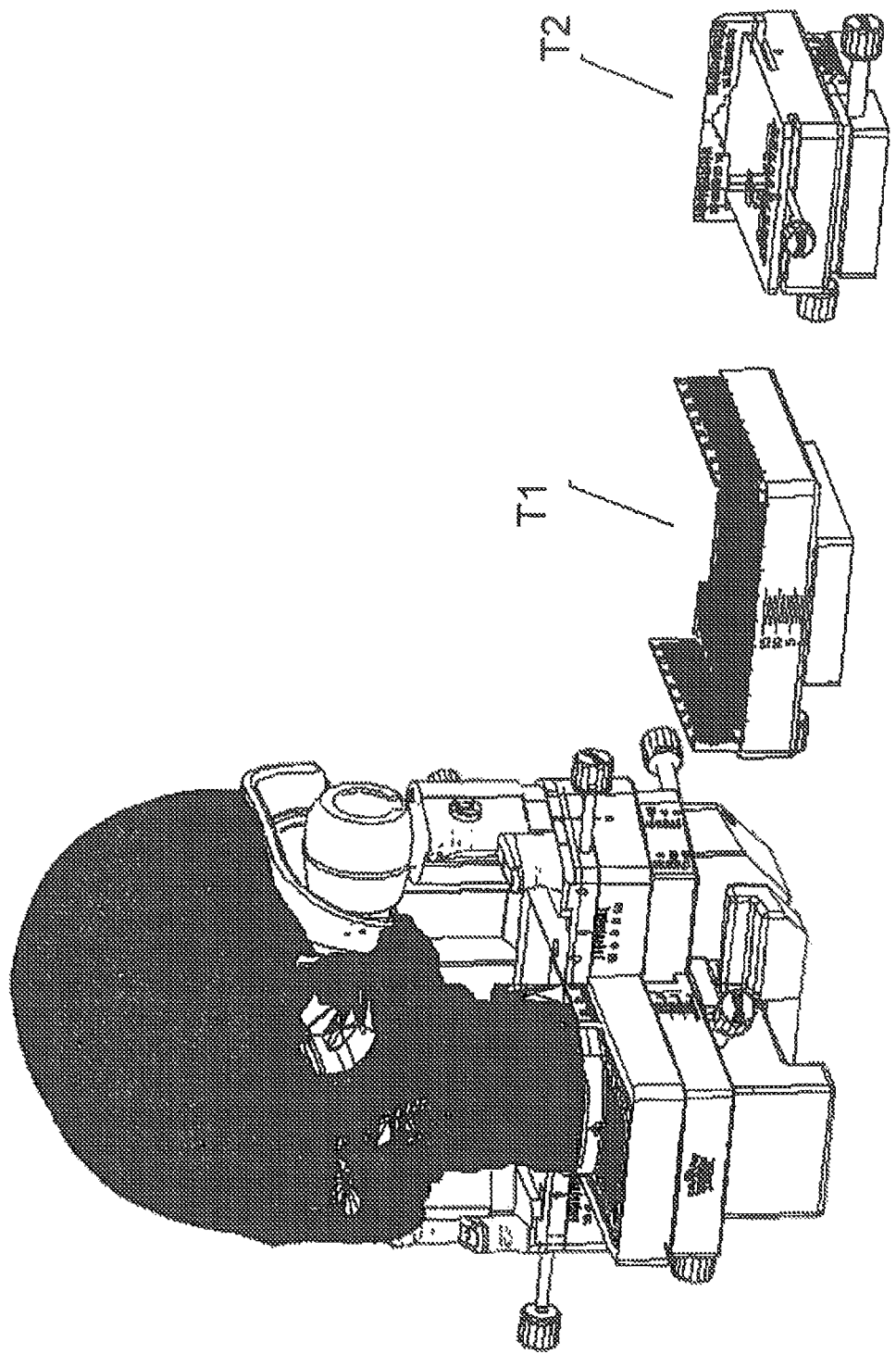
FIG. 2 is a perspective view of the articulator according to FIG. 1 with a skull dome in position, including an evaluating table and an articulating table used when applying a method according to a first aspect of the invention.
Figure 3:
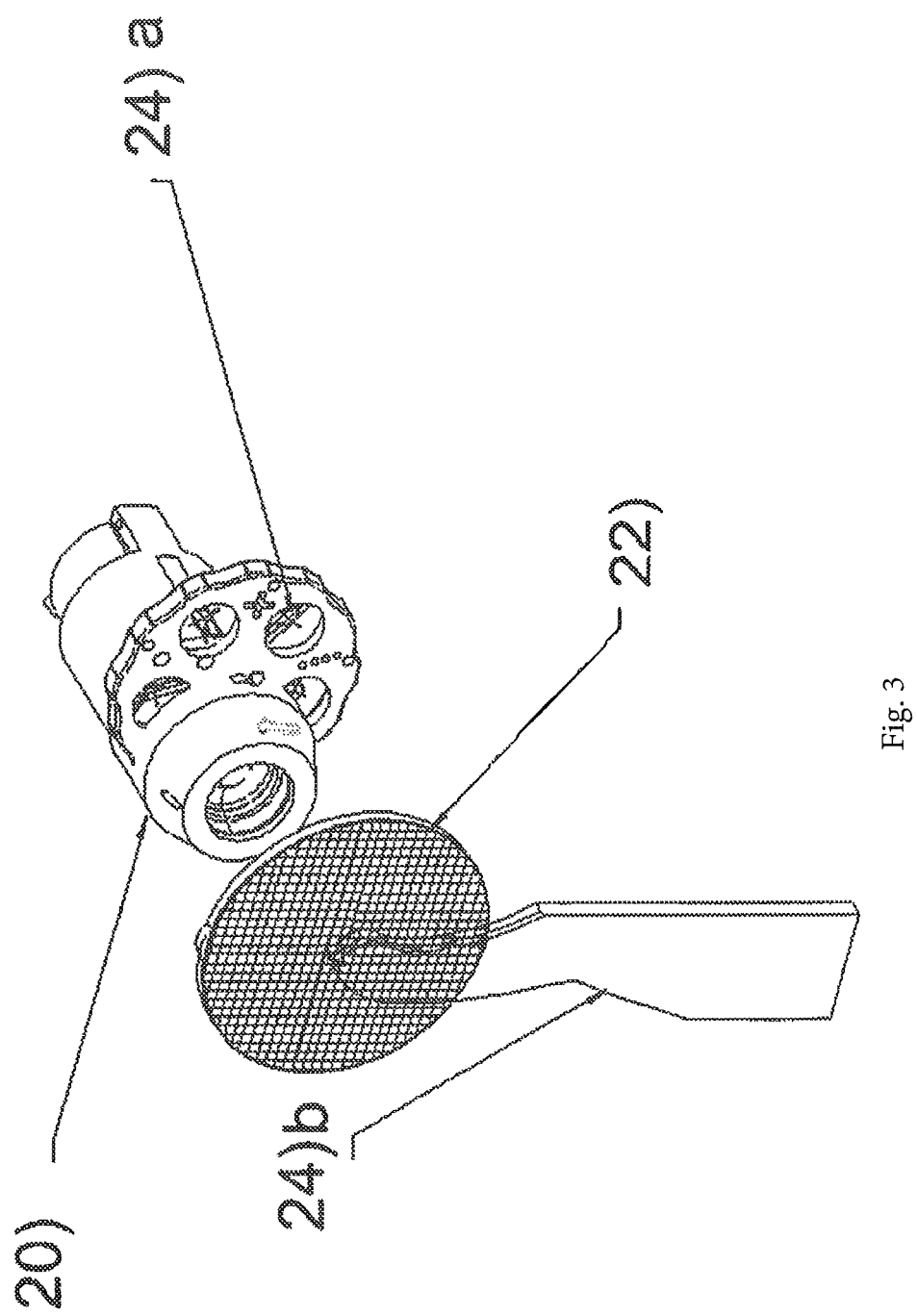
FIG. 3 is a perspective view of a light source, template, and grid forming part of the articulator in FIG. 1.
Figure 4:
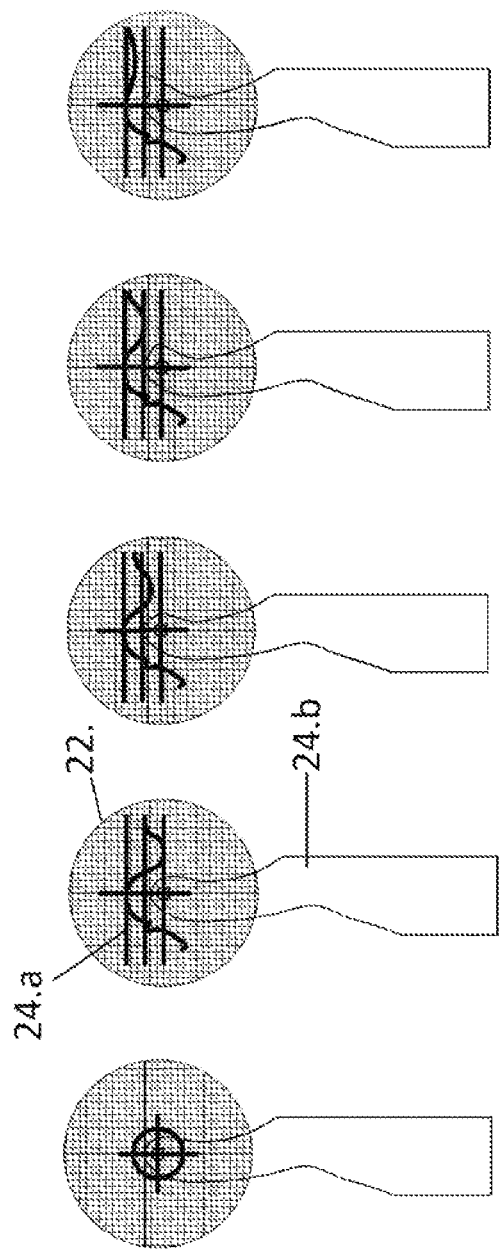
FIG. 4 illustrates the method according to a first aspect of the invention, showing five exemplary scenarios of fossae/eminence patterns displayed on a grid and cross hairs on the grid to determine the position of the condoylar head distance and position.
Figure 5:
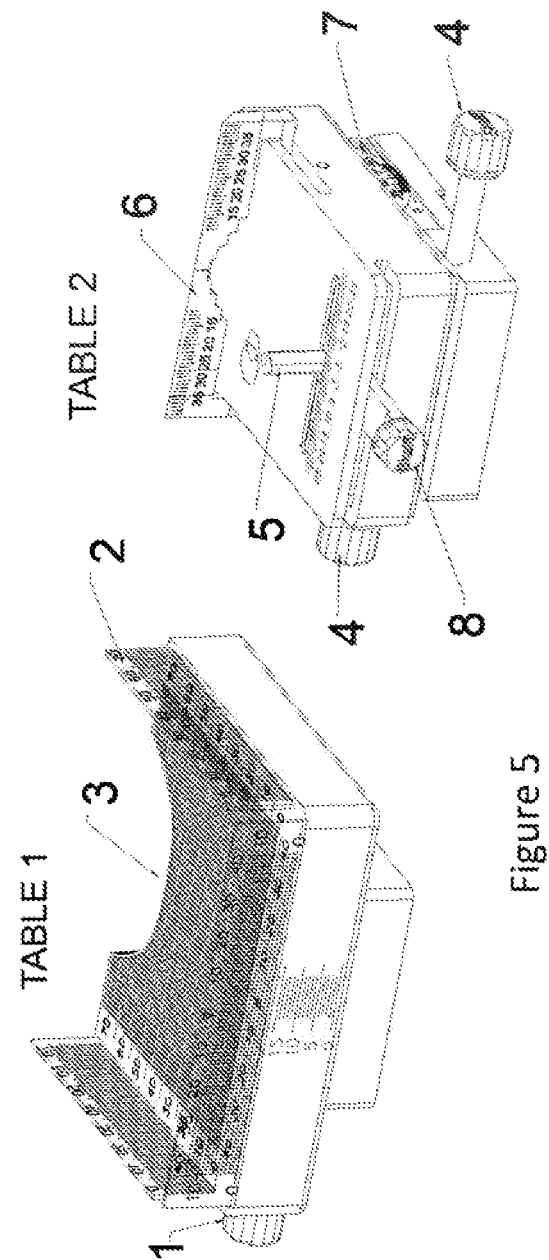
FIG. 5 is a perspective view of the tables in FIG. 2.

With reference to FIGS. 1 to 6 of the drawings, an articulator 10 includes a first mount 12 for receiving and mounting a lower jaw dentition model 14 thereto, a second mount 16 for receiving and mounting an upper jaw dentition model 18 thereto, a light source 20 (e.g. a laser or LED light), a grid 22 and a template 24.

The articulator 10 includes means 26 for setting/adjusting the relative positions of the first and second mounts 12 and 16/upper and lower jaw dentition models 14 and 18. Such means 26 permits relative:
(i) relative forward, backward, up, down, left and right movement; and
(ii) relative roll, yaw and pitch,
of the mounts 12 and 16/models 14 and 18.

Once set or adjusted, locking means (not shown) lock the mounts 12 and 16/models 14 and 18 in position.

The articulator 10 includes a hinge 28 for permitting the second mount 16 with upper jaw dentition model 18 on the one hand and the first mount 12 with lower jaw dentition model 14 on the other hand to be movable between: (a) a biting condition, in which the lower and upper dentition models 14 and 18 are in contact with each other; and (b) a displaced condition, in which the lower and upper dentition models 14 and 18 are sufficiently displaced from each other to permit a bite impression tray (not shown) to be inserted there between.

The light source 20 is positioned on the articulator 10 in such a manner that movement of the mounts 12 and 16 between the biting and displaced conditions does not cause the light source 20 to alter its position.

The grid 22 is associated with the light source 20, with the light source 20 directed at the grid 22 to cast light thereon. The position of the grid 22 and stencil 24b are impacted by movement of the mount 16 between the biting and the treatment/balanced position.

Preferably, the light source 20 includes a projector shield (not shown), which projector shield comprises an opaque body with a transparent portion/slit. In use, the projector shield is positioned in the path of light emitted by the light source 20, the projector shield causing the light source 20 to cast light on to the grid 22 in a shape dictated by the transparent portion/slit.

Preferably, the articulator 10 is provided with a set of projector shields representing a variety of: (i) common outlines of condylar heads; and/or (ii) common patterns and depths of fossae and eminance.

The light source 20 and grid 22 are arranged such that manipulation of the means 26 causes relative moment of the light source 20 and grid 22 corresponding to the relative consequential movement of the mounts 12 and 16/models 14 and 18.

The articulator 10 is also provided with a set of templates 24. Each template 24 is a transparent body with an opaque pattern thereon. Each template 24 within the set includes a pattern representing: (i) a common outline of condylar heads; and/or (ii) a common pattern and depth of fossae and eminance.

The articulator 10 includes a formation (preferably, on the grid 22) for releasably securing a template 24 in front of the grid 22.

Figure 6:
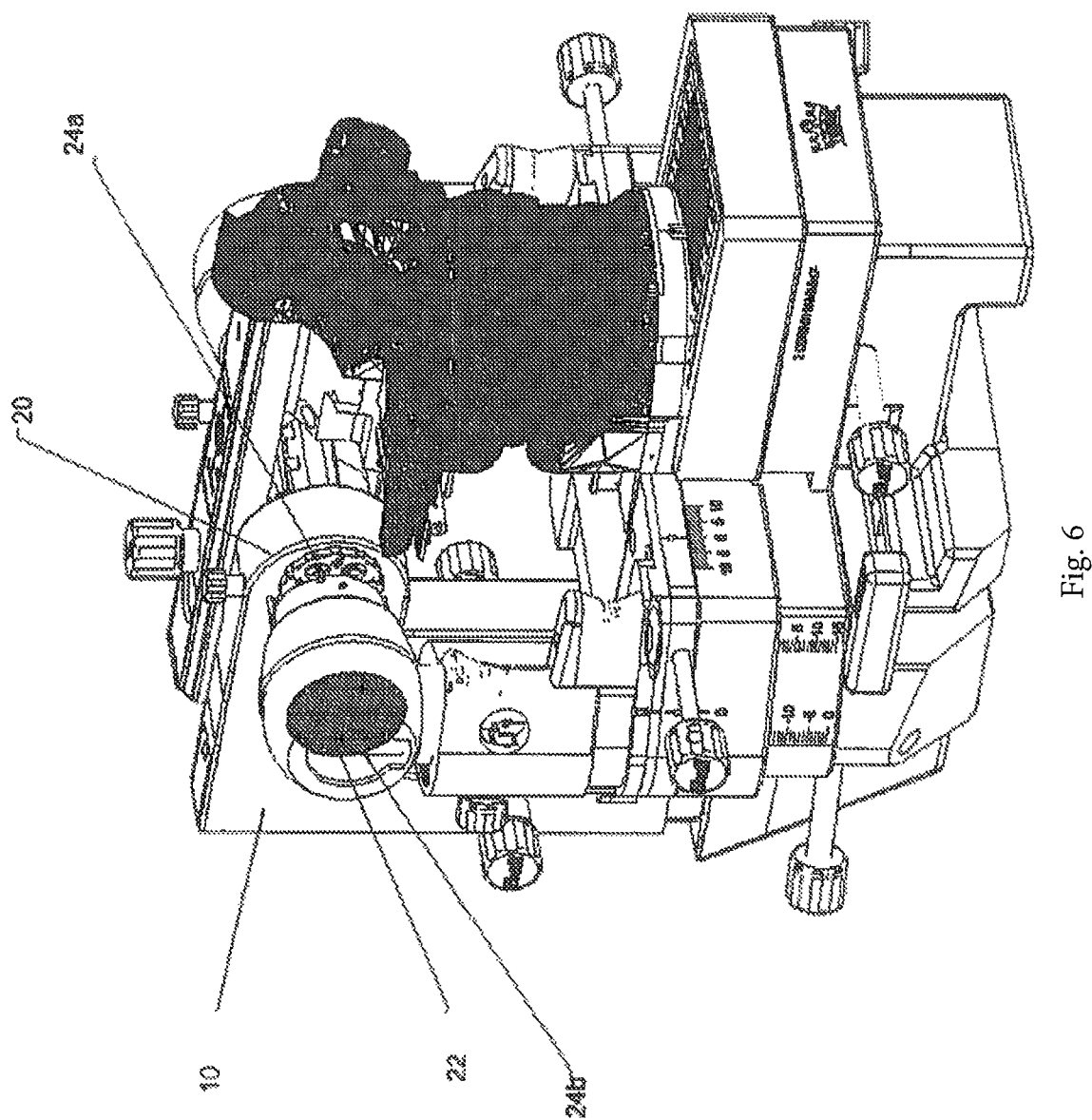
FIG. 6 is a perspective view of the articulator in FIG. 1 showing the actual position of the light source projector within the articulator.

FIG. 6 shows an evaluating table T1 and an articulating table T2. The evaluating table T1 is used to measure the size of the maxilla model for treatment purposes. In use, the evaluating table T1 is placed within the articulator 10 and an adjustment knob 1 may be rotated to set the height of the maxilla model. Replaceable rulers 2 may be used measure height and width of the maxilla model. The evaluating table surface defines measurements 3 for determining width and length of the maxilla model. The articulating table T2 used to mount the maxillary model within the articulator 10. The evaluating table T2 includes setting knobs 4 for adjusting angulation of the maxilla model, a pin 5 and a sliding gate 5 to position the maxilla model in the correct yaw, roll and pitch position. A built-in protractor 7 may be used to set the correct angulation according to the patient's scan/x-ray. The knobs 4 may be rotated adjust the position of maxilla model left/right and forwards/backwards.

The articulator 10 is used to determine treatment of orthopaedic imbalances in patients (not shown) using a method comprising the following steps:
1. mounting upper and lower jaw dentition models 14 and 18 to the articulator 10;
2. using the means 26 to set the position(s) of the upper and lower jaw dentition models 14 and 18 substantially to replicate the relative positions of the upper and lower jaw dentitions of a patient. The process of setting the models 14 and 18 typically comprises moving the models 14 and 18 forward, backward, up, down, left and right relative to each other; and causing relative roll, yaw and pitch of the models 14 and 18;
3. determining from one or more x-ray and/or scan of the patient's mandible and maxilla: (i) the outline of the patient's condylar head; and (ii) the pattern and depth of the patient's fossae; The articulator 10 is used to determine these measurements and set the 24b condoylar position and patterns of fossae/eminence 24a.
4. selecting a suitable representative projector shield or template 24 (i.e. a template stensil) for the outline of the patient's condylar head, and mounting the projector shield or template 24 to the articulator 10 so as to display a substantial reproduction of the outline of the patient's condylar head. Preferably, the outline of the patient's condylar head is displayed on the grid 22 using the light source 20 covered by a projector shield;
5. selecting a suitable representative projector shield or template 24 for the patient's fossae and eminance pattern and depth, and mounting the projector shield or template 24 to the articulator 10 so as to projection display a substantial reproduction of the pattern and depth of the patient's fossae and eminance. Preferably, the pattern shape depth of the patient's fossae and eminance is represented by a photo projection/template 24 that is secured to the grid 22 in overlapping configuration;
6. using the means 26 (in a similar manner as set out in step 2 above) to adjust the relative position of the upper and lower jaw dentition models 14 and 18 to determine the treatment of orthopaedic imbalances, which adjustment causes relative movement of: (i) the display of the condylar head outline; and (ii) the display of the pattern and depth of the fossae and eminance. The aim being to make such adjustments as are required to reduce/eliminate interference between the condylar head outline and fossae pattern and depth displayed on the articulator 10; and
7. recording the adjustments made to the relative position of the upper and lower jaw dentition models 14 and 18, which recordal is facilitated by taking readings from the grid 22.

It will be appreciated that a "substantial reproduction" is intended to mean a reproduction sufficiently close to the original to achieve effective results. Typically an accuracy rate of 95% is sufficient.

The position of the mounts 12 and 16 are then locked in position and the models 14 and 18 are moved from the biting condition to the desired treatment/balanced position. After inserting a bite impression tray between the models 14 and 18, the models 14 and 18 are returned to the biting condition to take an impression of the models 14 and 18 in their adjusted positions.

It will be appreciated that, by providing for both the condylar head outline and the fossae pattern and depth to be displayed on the articulator 10, the articulator 10 enables a user to view and record the impact that adjustments to relative positions of the models 14 and 18 has upon the relative position of the condylar head outline and fossae pattern and depth. It will be appreciated that this benefit facilitates improved determination of treatment of orthopaedic imbalances by dentists and dental surgeons.

It will also be appreciated that although, the upper and lower jaw dentition models 14 and 18 have been described as tangible models (e.g. 3D printed models):

(i) the upper and/or lower jaw dentition models 14 and 18, condoyle and eminance could be virtual models (e.g. holograms/projections), projected using projectors 30 shown in FIGS. 7(a)-(c). FIGS. 7(a)-(c) show three embodiments of adapters that can be mounted to the articulator 10. These adapters allow the practitioner/user to simulate the eminence and coldoyle by way of:
   3D printed parts, as shown in FIG. 7(a), which shows a mounted 3D printed eminence 24a and condoyle head 24b—the distance between the condoyle and the eminence is measured to determine treatment;
   3D holographic medical dicomm file, as shown in FIG. 7(b), which shows a holographic projector 32a projecting a 3D scanned eminence 24a horizontally, and a holographic projector 32b projecting the 3D condoylar head image 24b vertically—the distance between the condoyle and the eminence is measured to determine treatment; and
   2D image projection; as shown in FIG. 7(c), which shows a projector 32a and projector lens 34a to project the image of a 2D scanned eminence 24a horizontally, and a projector 32b projecting the 2D image of the condoylar head 24b against a 45 degrees grid lens 34b— the distance between the condoyle and the eminence is measured to determine treatment; and (ii) the upper and lower jaw dentition models 14 and 18, condoyle and eminance may be electronic models (e.g. 3D CAD models), and that the method steps claimed herein could be simulated electronically (e.g. using 3D CAD models of the upper and lower jaw dentition models 14 and 18, condoyle, eminance and articulator 10).

The invention claimed is:

1. A method for determining treatment of orthopaedic imbalances, the method including the steps of:
   mounting upper and lower jaw dentition models to an articulator;
   setting the position of the upper and lower jaw dentition models substantially to replicate the relative positions of the upper and lower jaw dentitions of a patient;
   determining from one or more x-ray or scan: (i) the outline of the patient's condylar head; and (ii) the pattern and depth of the patient's fossae;
   displaying a substantial reproduction of the outline of the patient's condylar head;
   displaying a substantial reproduction of the pattern and depth of the patient's fossae and eminance;
   adjusting the relative position of the upper and lower jaw dentition models to remedy orthopaedic imbalances, which adjustment causes relative movement of: (i) the display of the condylar head; and (ii) the display of the pattern and depth of the fossae and eminance; and
   recording the adjustments made to the relative position of the fossae/eminence and condoylar head and the upper and lower jaw dentition models.

2. A method according to claim 1, further including the step of taking an impression of the bite of the upper and lower jaw dentition models after the relative position of the upper and lower jaw dentition models have been adjusted.

3. A method according to claim 2, wherein the steps of: (i) setting the position of the upper and lower jaw dentition models substantially to replicate the relative positions of the upper and lower jaw dentitions of a patient; and (ii) adjusting the relative position of the upper and lower jaw dentition models to remedy orthopaedic imbalances, comprises relative forward, backward, up, down, left, right, roll, yaw and pitch of the upper and lower jaw dentition models.

4. A method according to claim 3, wherein templates are used to: (i) display a substantial reproduction of the outline of the patient's condylar head; and (ii) projection display the pattern and depth of the patient's fossae.

5. A method according to claim 4, wherein the outline of the patient's condylar head is displayed by a template stencil.

6. A method according to claim 5, wherein the step of displaying the pattern and depth of the patient's fossae comprises selecting from a series of photo projections pattern that best matches the pattern shape depth of the patient's fossae and securing the selected photo projection to the articulator.

7. A method according to claim 5, wherein the template patterns are printed on a transparent template body.

8. An articulator for use in determining treatment of orthopaedic imbalances, the articulator including:
   a light source;
   a grid on which the light source, in use, casts light; and
   a template that displays a shape representing: (i) the outline of a condylar head; or (ii) the pattern and depth of a fossae, which template is removably securable to the articulator.

9. An articulator according to claim 8, wherein the articulator includes mounts for securing upper and lower jaw dentition models thereto, and which articulator permits relative forward, backward, up, down, left, right, roll, yaw and pitch of the mounts.

* * * * *